US011820868B2

(12) United States Patent
Delaney, Jr. et al.

(10) Patent No.: US 11,820,868 B2
(45) Date of Patent: Nov. 21, 2023

(54) MULTIFUNCTIONAL NITROXIDE-MEDIATED POLYMERIZATION INITIATORS AND MULTI-ARMED POLYMERS AND HYDROGELS FORMED THEREFROM

(71) Applicant: Boston Scientific Scimed Inc., Maple Grove, MN (US)

(72) Inventors: Joseph T. Delaney, Jr., Minneapolis, MN (US); Paul V. Grosso, Maple Grove, MN (US); John Kummailil, Sherborn, MA (US); Tatyana Dyndikova, Minneapolis, MN (US); Carey Rehder, Inver Grove Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 379 days.

(21) Appl. No.: 16/999,822

(22) Filed: Aug. 21, 2020

(65) Prior Publication Data
US 2021/0061957 A1 Mar. 4, 2021

Related U.S. Application Data

(60) Provisional application No. 62/892,782, filed on Aug. 28, 2019.

(51) Int. Cl.
*C08F 283/12* (2006.01)
*C08G 77/04* (2006.01)
(Continued)

(52) U.S. Cl.
CPC .......... *C08G 77/045* (2013.01); *C08F 283/12* (2013.01); *A61L 27/52* (2013.01); *A61L 27/58* (2013.01)

(58) Field of Classification Search
CPC .................................................. C08F 2438/02
See application file for complete search history.

(56) References Cited

U.S. PATENT DOCUMENTS 6,818,018 B1 11/2004 Sawhney et al.
6,875,831 B1 4/2005 Kramer et al.
(Continued)

FOREIGN PATENT DOCUMENTS

WO 03/004471 * 1/2003

OTHER PUBLICATIONS

Lu et al. "Star Block Copolymers Through Nitroxide Mediated Radical Polymerization From Polyhedral Oligomeric Silsesquioxanes (POSS) Core". Macromolecular Chemistry and Physics, vol. 211, Issue 12, p. 1339-1247, Jun. 2010.*

(Continued)

*Primary Examiner* — Margaret G Moore
(74) *Attorney, Agent, or Firm* — Seager, Tufte & Wickhem LLP (57) ABSTRACT

In some aspects, the present disclosure pertains to multi-arm polymers that comprise a core and a plurality of polymer segments having a first end that is covalently attached to the core and (a) a second end comprising a moiety that comprises a reactive end group, wherein the polymer segments comprise one or more hydrophilic aprotic NMP-polymerizable monomers, and wherein the reactive multi-arm polymer comprises nitroxide radicals or (b) a second end comprising a moiety that comprises an alkoxyamine group, wherein the core is a polyol residue, and wherein the polymer segments comprise one or more NMP-polymerizable monomers. In some aspects, the present disclosure pertains to a multifunctional alkoxyamine molecule comprising a core and a plurality of alkoxyamine groups covalently attached to the core, wherein the core is a polyol residue.

11 Claims, 2 Drawing Sheets

(51) Int. Cl.
A61L 27/52 (2006.01)
A61L 27/58 (2006.01)

(56) References Cited

U.S. PATENT DOCUMENTS

| | | |
|---|---|---|
| 8,383,161 B2 | 2/2013 | Campbell et al. |
| 2005/0065119 A1 | 3/2005 | Couturier et al. |
| 2011/0142936 A1 | 6/2011 | Campbell et al. |
| 2013/0030071 A1* | 1/2013 | Kou .......................... C08F 8/42 525/308 |

OTHER PUBLICATIONS

Sinoj Abraham et al., "Synthesis of star polymers via nitroxide mediated free radical polymerization: A "cor-first" approach using resorcinarene-based alkoxyamine initiators", Journal of Polymer Science Part A: Polymer Chemistry, vol. 45, No. 23, Oct. 22, 2007, pp. 5559-5572.

Dufils et al., "Intermolecular radical addition of alkoxyamines onto olefines: An easy access to advanced macromolecular architecture precursors", Polymer, Elsevier Science Publishers B.V, Gb, vol. 48, No. 18, Aug. 16, 2007, pp. 5219-5225.

Dufils P-E et al., "One Step Synthesis of NMP Star Polymer Initiator for "Core First" Method" Polymer Preprints, American Chemical Society, US, vol. 46, No. 2, Jan. 1, 2005, pp. 328-329.

International Search Report and Written Opinion for the Application No. PCT/US2020/047436, dated Oct. 23, 2020, 16 pages.

Zhang, P.; Sun, F.; Liu, S.; Jiang, S., Anti-PEG antibodies in the clinic: Current issues and beyond PEGylation. J. Control. Release 2016, 244 (Pt B), 184-193.

"Augmenix Announces Positive Three-year SpaceOAR Clinical Trial Results," Imaging Technology News, Oct. 27, 2016.

"Augmenix Receives FDA Clearance to Market its TraceIT™ Tissue Marker," BusinessWire Jan. 28, 2013.

* cited by examiner

MULTIFUNCTIONAL NITROXIDE-MEDIATED POLYMERIZATION INITIATORS AND MULTI-ARMED POLYMERS AND HYDROGELS FORMED THEREFROM

CROSS-REFERENCE TO RELATED APPLICATION

This application claims the benefit of U.S. Provisional Application No. 62/892,782, entitled "MULTIFUNCTIONAL NITROXIDE-MEDIATED POLYMERIZATION INITIATORS AND MULTI-ARMED POLYMERS AND HYDROGELS FORMED THEREFROM" and filed Aug. 28, 2019, the entire disclosure of which is incorporated herein by reference.

FIELD

The present disclosure relates to multifunctional nitroxide-mediated polymerization initiators, multi-armed polymers formed therefrom, and compositions and systems containing such multi-armed polymers, among other aspects. The multi-armed polymers of the present disclosure are useful, for example, in various medical applications including pharmaceutical and medical device applications.

BACKGROUND

Nitroxide-mediated radical polymerization is a method of radical polymerization that makes use of alkoxyamine initiators to generate polymers with well controlled stereochemistry and a very low polydispersity. Such polymers are potentially useful in a number of fields including the biomedical field.

The present disclosure pertains to novel multifunctional nitroxide-mediated polymerization initiators, to multi-armed polymers formed therefrom and to compositions and systems containing such multi-armed polymers, among other aspects.

SUMMARY

In some aspects, the present disclosure pertains to multi-arm polymers that comprise a core and a plurality of polymer segments having a first end that is covalently attached to the core and a second end comprising a moiety that comprises a reactive end group, wherein the polymer segments comprise one or more hydrophilic aprotic NMP-polymerizable monomers, and wherein the reactive multi-arm polymer comprises nitroxide radicals.

In some embodiments, the core is selected from a polyol residue and a silsesquioxane core.

In some embodiments, which may be used in conjunction with the above aspects and embodiments, the reactive end group may be an electrophile or a nucleophile.

In some embodiments, which may be used in conjunction with the above aspects and embodiments, the moiety that comprises a reactive end group may further comprise a hydrolysable ester group.

In some aspects, the present disclosure pertains to a system comprising (a) a first composition comprising a multi-arm polymer in accordance with any of the above aspects and embodiments and (b) a second composition comprising a multifunctional compound that comprises functional groups that are reactive with the reactive end groups of the multi-arm polymer.

In some embodiments, the system comprises a delivery device.

In some aspects, the present disclosure pertains to cross-linked reaction product of (a) a multi-arm polymer in accordance with any of the above aspects and embodiments and (b) a multifunctional compound that comprises functional groups that are reactive with the reactive end groups of the multi-arm polymer.

In some aspects, the present disclosure pertains to a multi-arm polymer comprising a core and a plurality of polymer segments each having a first end that is covalently attached to the core and a second end comprising a moiety that comprises an alkoxyamine group, wherein the core is a polyol residue, and wherein the polymer segments is formed from one or more NMP-polymerizable monomers.

In some embodiments, the polymer segments are formed from one or more NMP-polymerizable hydrophilic aprotic monomers.

In some embodiments, the polymer segments formed from monomers comprising N-vinyl pyrrolidone.

In some embodiments, which may be used in conjunction with the above aspects and embodiments, the polyol residue may be is a residue of a polyol selected from straight-chained, branched and cyclic aliphatic polyols, straight-chained, branched and cyclic polyhydroxy ethers, straight-chained, branched and cyclic polyhydroxy polyethers, straight-chained, branched and cyclic polyhydroxyalkyl ethers, and straight-chained, branched and cyclic polyhydroxyalkyl polyethers.

In some embodiments, which may be used in conjunction with the above aspects and embodiments, the polyol residue may be a residue of a polyol selected from sugars, sugar alcohols, sugar oligomers, sugar alcohol oligomers, sugar polymers, and sugar alcohol polymers.

In some embodiments, which may be used in conjunction with the above aspects and embodiments, the polyol residue may comprise an ether or polyether.

In some embodiments, which may be used in conjunction with the above aspects and embodiments, the plurality of alkoxyamine groups comprise four alkyl groups attached to two carbons atoms in $\alpha$-positions relative to the alkoxyamine group nitrogen atom.

In some embodiments, which may be used in conjunction with the above aspects and embodiments, the plurality of alkoxyamine groups are cyclic alkoxyamine groups.

In some embodiments, which may be used in conjunction with the above aspects and embodiments, the plurality of alkoxyamine groups comprise 1,1,3,3-tetramethylisoindolin-2-yloxyl (TMIO) groups.

In some aspects, the present disclosure pertains to a multifunctional alkoxyamine molecule comprising a core and a plurality of alkoxyamine groups covalently attached to the core, wherein the core is a polyol residue.

In some embodiments, the polyol residue may be a residue of a polyol selected from straight-chained, branched and cyclic aliphatic polyols, straight-chained, branched and cyclic polyhydroxy ethers, straight-chained, branched and cyclic polyhydroxy polyethers, straight-chained, branched and cyclic polyhydroxyalkyl ethers, and straight-chained, branched and cyclic polyhydroxyalkyl polyethers.

In some embodiments, which may be used in conjunction with the above aspects and embodiments, the polyol residue may be a residue of a polyol selected from sugars, sugar alcohols, sugar oligomers, sugar alcohol oligomers, sugar polymers, and sugar alcohol polymers.

In some embodiments, which may be used in conjunction with the above aspects and embodiments, the polyol residue may comprise an ether or polyether.

In some embodiments, which may be used in conjunction with the above aspects and embodiments, the plurality of alkoxyamine groups may be covalently attached to the core via an ester linkage.

In some embodiments, which may be used in conjunction with the above aspects and embodiments, the plurality of alkoxyamine groups comprise four alkyl groups attached to two carbons atoms in α-positions relative to the alkoxyamine group nitrogen atom.

In some embodiments, which may be used in conjunction with the above aspects and embodiments, the plurality of alkoxyamine groups are cyclic alkoxyamine groups.

In some embodiments, which may be used in conjunction with the above aspects and embodiments, the plurality of alkoxyamine groups comprise 1,1,3,3-tetramethylisoindolin-2-yloxyl (TMIO) groups.

In some aspects, the present disclosure pertains to methods of forming a multifunctional alkoxyamine molecule in accordance with the above aspects and embodiments, the methods comprising (a) reacting hydroxyl groups of a polyol with an α-halogenated-$C_2$-$C_6$ acid halide to form an intermediate compound, followed by reaction of the intermediate compound with a nitroxide radical in a nitroxide radical coupling step to form a multifunctional alkoxyamine molecule.

These and other aspects and embodiments of the present disclosure will become readily apparent to those of ordinary skill in the art upon review of the Detailed Description to follow.

DETAILED DESCRIPTION

In various aspects of the present disclosure, multifunctional alkoxyamine molecules are provided that comprise a core and a plurality of alkoxyamine groups attached to said core. In various embodiments, the alkoxyamine group comprises a cyclic alkoxyamine group, such as a monocyclic or a multicyclic alkoxyamine group. In various embodiments, four alkyl groups (e.g., methyl, ethyl, n-propyl, isopropyl, n-butyl, isobutyl, t-butyl, etc.) are attached to two carbons atoms in α-positions relative to the nitrogen atom of the alkoxyamine group. In various embodiments, the alkoxyamine groups is an acyclic alkoxyamine group. In various embodiments, the alkoxyamine group is a cyclic or acyclic alkoxyamine group in which four alkyl groups are attached to two carbons atoms in α-positions relative to the nitrogen atom of the alkoxyamine group. Such multifunctional alkoxyamine molecules are useful, for example, as multifunctional initiator molecules for the formation of multi-arm polymers by nitroxide-mediated polymerization (NMP) of at least one type of unsaturated free-radical-polymerizable monomer.

In various embodiments, multifunctional alkoxyamine molecules are provided in which the core is a polyol residue. For example, multifunctional alkoxyamine molecules may be prepared by esterification of a polyol with an alpha-halogenated acid halide, for example, an alpha-halogenated $C_2$-$C_6$ acid halide, preferably an alpha-bromo-acid bromide, for example, an alpha-bromo-$C_2$-$C_6$-acid bromide, followed by coupling with a nitroxide radical to form a plurality of substituted alkoxyamine end groups.

Illustrative alpha-halogenated $C_2$-$C_6$ acid halides include, for example, bromoacetyl bromide, 2-bromopropionyl bromide, 2-bromobutyryl bromide, or 2-bromoisobutyryl bromide, among others.

Illustrative polyols for use in forming alkoxyamine molecules include, for example, straight-chained, branched and cyclic aliphatic polyols including straight-chained, branched and cyclic polyhydroxyalkanes, straight-chained, branched and cyclic polyhydroxy ethers and polyhydroxy polyethers, straight-chained, branched and cyclic polyhydroxyalkyl ethers and polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, or maltose, oligomers (defined herein as ranging from two to ten units, including dimers, trimers, tetramers, pentamers, hexamers, heptamers, octamers, enneamers or decamers) and polymers (defined herein as eleven or more units) of straight-chained, branched and cyclic sugars and sugar alcohols, including the preceding sugars and sugar alcohols, starches, amylose, dextrins, cyclodextrins, polyhydroxy crown ethers, or polyhydroxyalkyl crown ethers, and aromatic polyols including 1,1,1-tris(4'-hydroxyphenyl) alkanes, such as 1,1,1-tris(4-hydroxyphenypethane, and 2,6-bis(hydroxyalkyl)cresols, among others. In certain preferred embodiments, the polyol is an oligomer of a sugar alcohol such as glycerol, mannitol, sorbitol, inositol, xylitol, or erythritol. In certain preferred embodiments, a polyol may be selected which contains two or more hydroxyl groups, for example, between 3 and 12 hydroxyl groups in certain instances.

In various embodiments, the nitroxide radical is a cyclic nitroxide radical, such as a monocyclic and multicyclic nitroxide radical. In various embodiments, four alkyl groups (e.g., methyl, ethyl, n-propyl, isopropyl, n-butyl, isobutyl, t-butyl, etc.) are attached to two carbons atoms in α-positions relative to the nitrogen atom of the nitroxide radical. In various embodiments, the nitroxide radical is an acyclic nitroxide radical. In various embodiments, the nitroxide radical is a cyclic or acyclic nitroxide radicals in which four alkyl groups are attached to two carbons atoms in α-positions relative to the nitrogen atom of the nitroxide radical. Specific examples, include monocyclic nitroxide radicals such as 2,2,6,6-tetramethylpiperidine-1-oxyl (TEMO) and derivatives such as 4-oxo-2,2,6,6-tetramethyl-1-piperidinyloxy (4-oxo-TEMPO), 4-Hydroxy-2,2,6,6-tetramethylpiperidine-1-oxyl (TEMPOL), 4-Amino-2,2,6,6-tetramethylpiperidine-1-oxyl (4-amino-TEMPO), 4-acetamido-2,2,6,6-tetramethylpiperidine 1-oxyl (4-acetamido TEMPO), 4-maleimido-2,2,6,6-tetramethyl-1-piperidinyloxy (4-Maleimido-TEMPO), and 4-Hydroxy-2,2,6,6-tetramethylpiperidine 1-oxyl benzoate (4-Hydroxy-TEMPO benzoate), 2,2,5,5-tetramethylpyrroline-1-oxyl and derivatives such as 3-carbamoyl-2,2,5,5-tetramethyl-3-pyrrolin-1-oxyl, 2,2,5,5-tetramethylpyrrolidine-1-oxyl and derivatives such as 2,2,5,5-tetramethylpyrrolidine-3-carboxamide, 2,2,5,5-tetramethylimidazoline-1-oxyl and derivatives such as 2-phenyl-4,4,5,5-tetramethylimidazoline-1-oxyl 3-oxide (PTIO), 2,2,5,5-tetramethylimidazolidin-1-oxyl and derivatives such as 4-phenacylidene-2,2,5,5-tetramethylimidazolidin-1-yloxy, and bicyclic nitroxide radicals such as and for example, 1,1,3,3-tetramethylisoindolin-2-yloxyl (TMIO) (CAS 80037-90-7), 1,1,3,3-tetraethylisoindolin-2-yloxyl (TEISO) and derivatives such as 5-acetamido-1,1,3,3-tetramethylisoindolin-2-yloxyl, and 5-amino-1,1,3,3-tetramethylisoindolin-2-yloxyl, and an SG1 radical, among others.

Figure 1:
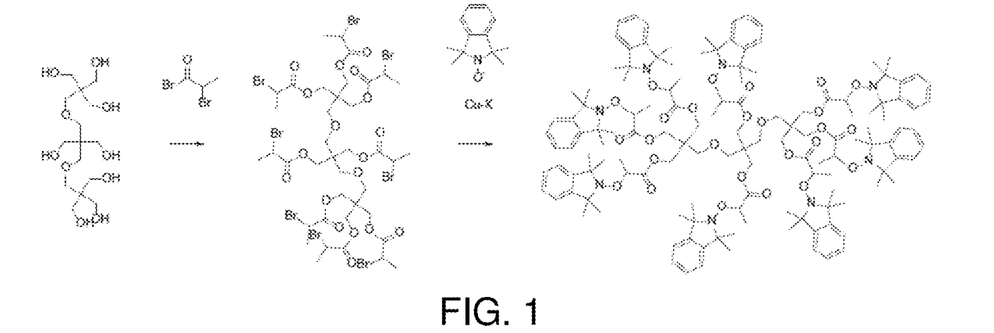
FIG. 1 is a schematic illustration of a method of forming a multi-functional nitroxide molecule from a polyol precursor molecule, in accordance with an embodiment of the present disclosure.

In a specific example shown in FIG. 1, an octanol, specifically, tripentaerythritol, is esterified of using 2-bromopropionyl bromide, followed by copper-catalyzed nitroxide radical coupling with 1,1,3,3-tetramethyl isoindolin-N-oxyl to produce an octa-functional alkoxyamine molecule that comprises a tripentaerythritol residue core and a plurality of alkoxyamine groups, specifically, TMIO groups attached to the core.

In various embodiments, multifunctional alkoxyamine molecules may also be provided that comprise a silsesquioxane core and a plurality of alkoxyamine groups attached to the core. As used herein, the term silsesquioxane core refers to organosilicon core having the chemical formula $[SiO_{3/2}]_n$, wherein n is an integer, typically an integer of 6 or more. In various embodiments, n is 6, 8, 10 or 12. In this regard, examples of silsesquioxanes include silsesquioxanes having a ladder structure, silsesquioxanes having a T8 cage structure, silsesquioxanes having a T10 cage structure, silsesquioxanes having a T12 cage structure, and silsesquioxanes having a partial cage structure, among others.

Multifunctional nitroxide molecules may be prepared from silsesquioxanes having the formula $[RSiO_{3/2}]_n$, where n is an integer and R=H, alkoxyl, or aminoalkyl.

Figure 2:
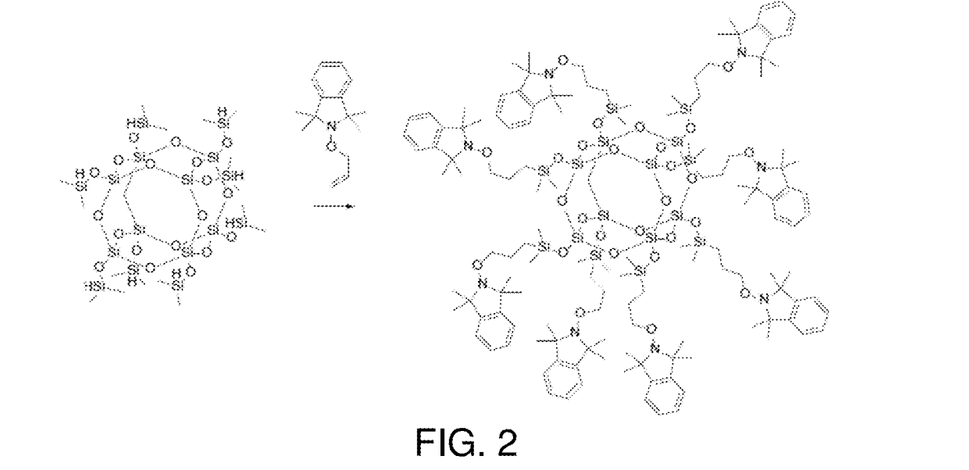
FIG. 2 is a schematic illustration of a method of forming a multi-functional nitroxide molecule from a polyhedral oligomeric silsesquioxane (POSS) precursor molecule, in accordance with an embodiment of the present disclosure.

For example, in some embodiments, a silsesquioxane silylhydride (where R=H) is reacted with an unsaturated nitroxide, for example, an allyl substituted nitroxide such as allyl TIMIO. For instance, in the particular example shown in FIG. 2, polyhedral oligomeric silsesquioxane (POSS) hydride, specifically octakis(dimethylsiloxy)silsesquioxane hydride $Q_8M_8^H$, is reacted with an allyl substituted nitroxide, specifically allyl TIMIO, to form an octa-functional alkoxyamine molecules that comprises a POSS residue core and eight alkoxyamine groups.

Figure 3:
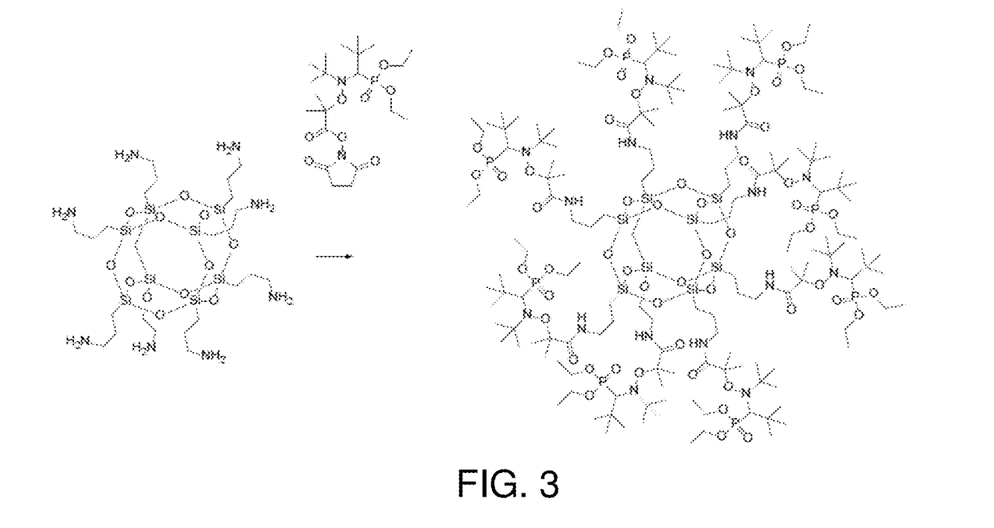
FIG. 3 is a schematic illustration of a method of forming a multi-functional nitroxide molecule from a POSS precursor molecule, in accordance with another embodiment of the present disclosure.

Multifunctional nitroxide molecules may also be prepared from an aminoalkyl silsesquioxane (where R=aminoalkyl, for example, $C_1$ to $C_8$ aminoalkyl, typically, aminomethyl, aminoethyl, aminopropyl or aminobutyl, etc.). For instance, an aminoalkyl silsesquioxane may be reacted with an N-hydroxy-succinimide (NHS)-functionalized alkoxyamines to form a multifunctional nitroxide molecule. In one particular example shown in FIG. 3, octa(aminopropyl)silsesquioxane (OAP-POSS) is reacted with an NHS-functionalized SG1 (N-tert-butyl-N-[1-diethylphosphono-(2,2-di methyl propyl)] nitroxide) to form an octa-functional alkoxyamine molecule that comprises a POSS core and eight alkoxyamine groups.

The above and other multifunctional alkoxyamine molecules may be useful, for example, as multifunctional initiator molecules for the formation of multi-arm polymers via nitroxide-mediated polymerization (NMP) of at least one type of unsaturated free-radical-polymerizable monomer.

Unsaturated free-radical-polymerizable monomers for use in the present disclosure may be selected, for example, from NMP-polymerizable-members of the following list, among others: (a) vinyl monomers, including vinyl pyrrolidone, vinyl alcohol (hydrolyzed vinyl acetate), halogenated vinyl compounds such as vinyl chloride and vinyl fluoride, vinyl imidazole, vinyl ethers, vinyl esters such as vinyl acetate, acrylonitrile, and vinyl aromatic monomers such as substituted and unsubstituted styrene, (b) alkylene monomers and derivatives, such as ethylene, propylenes (e.g., α-propylene, isopropylene), butylenes (e.g., α-butylene, β-butylene, isobutylene), pentenes, etc., (c) fluorinated unsaturated monomers including fluorinated alkylene monomers (e.g., tetrafluoroethylene, triflourochloroethylene, vinylidene fluoride, etc.), (d) (meth)acrylic monomers and derivatives, such as acrylic acid, methacrylic acid, methyl acrylate, methyl methacrylate, ethyl acrylate, ethyl methacrylate, butyl acrylate, butyl methacrylate, hydroxyethyl acrylate, hydroxyethyl methacrylate, glyceryl acrylate, glyceryl methacrylate, dimethylaminoethyl acrylate, dimethylaminoethyl methacrylate, PEG acrylates and PEG methacrylates, for example, PEG methyl ether acrylate and PEG methyl ether methacrylate, acrylamide, methacrylamide, ethacrylamide, and so forth, (e) nitriles including acrylonitrile, and methacrylonitrile, (f) diene monomers such as 1,3-butadiene, chloroprene, and isoprene, and (g) maleic anhydride, as well as combinations of the foregoing monomers.

In particular embodiments, the unsaturated free-radical-polymerizable monomers are selected from monomers which are hydrophilic, aprotic, biologically well-tolerated and can be polymerized via a living polymerization reaction mechanism, which allows for controlled polymer architecture.

In particular embodiments, the unsaturated free-radical-polymerizable monomers are selected from N-vinyl pyrrolidone, vinyl acetate (which can be hydrolyzed after polymerization to form vinyl alcohol), hydroxyethyl acrylate, hydroxyethyl methacrylate, PEG methyl ether acrylate, and PEG methyl ether methacrylate, among others.

Using the above and other techniques, a multi-arm polymer (e.g., one having 2, 3, 4, 5, 6, 7, 8, 9, 10 or more arms) with alkoxyamine end-groups can be formed. Using the above and other techniques, a multi-arm polymer that comprises a core (e.g., a polyol residue core or a silsesquioxane core) and a plurality of polymer segments, each having a first end and a second end, and each formed from polymerization of at least one type of unsaturated NMP-polymerizable monomer, wherein the first end is linked to the core and the second end is linked to an alkoxyamine group can be formed.

Figure 4A:
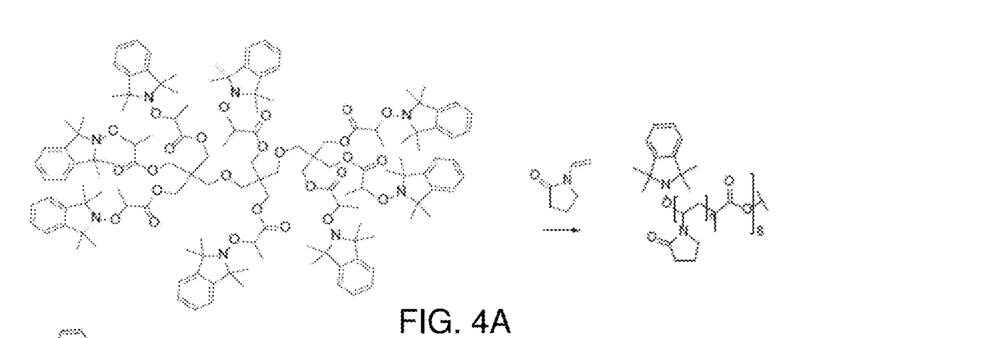
FIG. 4A is a schematic illustration of a method of forming a multi-arm poly(vinyl pyrrolidone) polymer having terminal nitroxide groups, in accordance with an embodiment of the present disclosure.

In a particular example illustrated in FIG. 4A, the octa-functional alkoxyamine molecule product of FIG. 1 is employed as an initiator for the nitroxide-mediated polymerization of N-vinyl pyrrolidone, to form an eight-arm poly(N-vinyl pyrrolidone) (PVP) molecule having a polyol residue core (i.e., a tripentaerythritol residue core) and alkoxyamine end groups (i.e., TMIO groups). (It is noted that the product of FIG. 4A is shown generically with only one arm (of eight) and only a portion of a generic core.) Similarly, the octa-functional alkoxyamine molecule of FIG. 2 or FIG. 3 may also be employed as an initiator for nitroxide-mediated polymerization of N-vinyl pyrrolidone, to form an eight-arm poly(N-vinyl pyrrolidone) (PVP) molecule having a silsesquioxane core and alkoxyamine end groups including the TMIO-based groups of FIG. 2 and the SG1-based groups of FIG. 3.

Figure 4B:
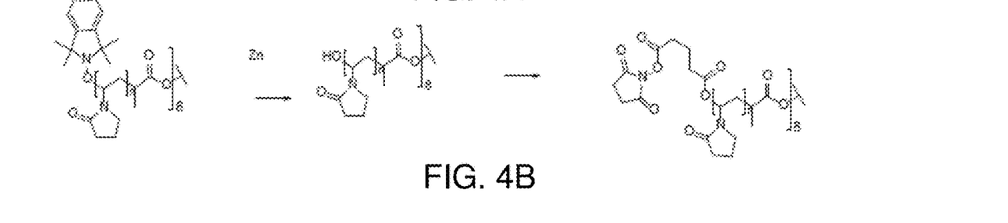
FIG. 4B is a schematic illustration of a method of forming a multi-arm poly(vinyl pyrrolidone) terminated with reactive succinimidyl glutarate groups, in accordance with an embodiment of the present disclosure.

After polymerization, in various embodiments, the alkoxyamine end groups may be removed to form, for example, a hydroxy-terminated multi-armed polymer. In certain embodiments, the alkoxyamine groups may be removed by reduction to hydroxyl groups, for example, using zinc as shown in FIG. 4B. The hydroxy-terminated multi-armed polymer will also contain nitroxide radicals as a result of the method by which it is produced, in some embodiments.

Figure 5:
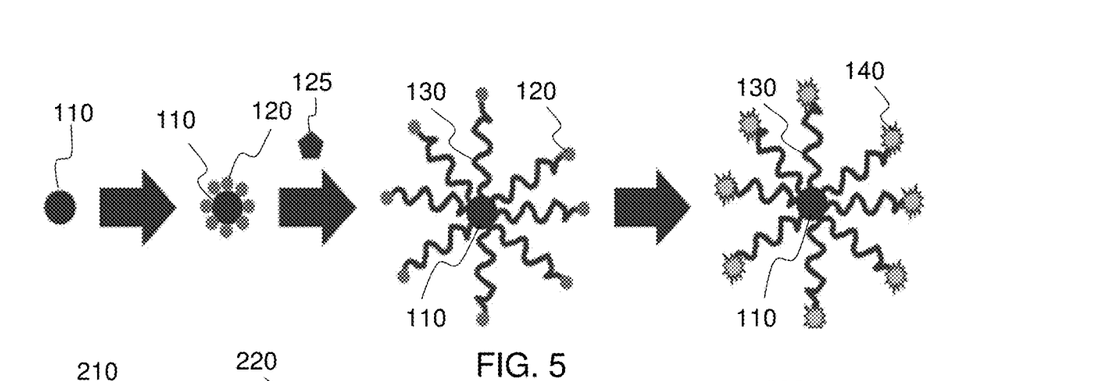
FIG. 5 is a schematic illustration of a method of making a reactive multi-arm polymer, in accordance with an embodiment of the present disclosure.

The formation of such multi-arm polymers is also shown schematically in FIG. 5, in which a core molecule 110 (e.g., a polyol residue core or a silsesquioxane core, among other possibilities) is used to form a multifunctional initiator molecule having a multiple polymerization groups 120 (e.g., an initiator molecule comprising multiple alkoxyamine groups). Subsequently, polymerization of a suitable NMP-polymerizable monomer 125 (e.g., a hydrophilic, aprotic, monomer such as vinyl pyrrolidone, among others) proceeds from the multifunctional initiator molecule to form a multi-arm polymer that comprises a core 110 (e.g., a polyol residue core or a silsesquioxane core) and a plurality of polymer segments 130 (e.g., PVP segments), each having a first end and a second end, wherein the first end is linked to the core 110. In the embodiment shown, the second end of each polymer segment 130 comprises a nitroxide polymerization group 120 (e.g., an alkoxyamine group).

In various embodiments, a reactive multi-arm polymer that comprises a core (e.g., a polyol residue core or a silsesquioxane core, among others) and a plurality of polymer segments, each having a first end and a second end, and each formed from at least one type of unsaturated NMP-polymerizable monomer may be formed, wherein the first end is linked to the core and the second end comprises a reactive group. For example, as shown schematically in FIG. 5, a reactive group 140 may be provided at the second end of each polymer segment 130. In certain embodiments, the second end comprises a hydrolysable ester group positioned between the reactive group and the polymer segment. The reactive multi-arm polymer may also contain nitroxide radicals as a result of the method by which it is produced, in some embodiments.

The reactive groups of the reactive multi-arm polymer may be, for example, electrophilic groups or nucleophilic groups. In certain embodiments, the reactive groups of the reactive multi-arm polymer may be electrophilic groups selected from imidazole esters, imidazole carboxylates, benzotriazole esters, and imide esters, including N-hydroxysuccinimidyl esters. In certain embodiments, the reactive groups of the reactive multi-arm polymer may be nucleophilic groups selected from amine groups and/or thiol groups.

In particular embodiments, a reactive multi-arm polymer may be formed by reacting (a) a polymer that comprises a core (e.g., a polyol residue core or a silsesquioxane core, among others) and a plurality of polymer segments, each having a first end and a second end, formed from at least one type of unsaturated NMP-polymerizable monomer, wherein the first end is linked to the core and the second end comprises a hydroxyl group (e.g., after removal of alkoxyamine groups by reduction to hydroxyl groups as described above) with (b) a cyclic anhydride (e.g., glutaric anhydride, succinic anhydride, malonic anhydride, etc.) to form a reaction product (c) in the form of a polymer that comprises the core and the plurality of polymer segments, wherein the first end of the polymer segment is linked to the core and the second end comprises moiety that comprises a carboxylic acid group and a hydrolysable ester group positioned between the carboxylic acid group and the polymer segment. Subsequently, the reaction product (c) may be treated with a coupling agent (e.g., a carbodiimide coupling agent such as N,N'-dicyclohexylcarbodiimide (DCC), 1-Ethyl-3-(3-dimethylaminopropyl)carbodiimide (EDC), N-Hydroxybenzotriazole (HOBt), BOP reagent, and/or another coupling agent) and N-hydroxysuccinimde (NHS), to yield a multi-arm polymer comprising succinimidyl end groups, in particular, a multi-arm polymer that comprises the core and the plurality of polymer segments, wherein the first end of the polymer segments is linked to the core and the second end comprises a moiety that comprises a hydrolysable ester group and a succinimide ester group.

Reactive multi-arm polymers formed as described above may be water soluble. Moreover, multi-arm polymers formed as described above may be crosslinked with a suitable crosslinking agent, either in vivo or ex vivo, to form a crosslinked hydrogel. As noted above, reactive multi-arm polymers may also contain nitroxide radicals as a result of the method by which they are produced, in some embodiments.

In certain embodiments, the reactive multi-arm polymer may be crosslinked with a multifunctional compound having functional groups that are reactive with the reactive groups of the multi-arm polymer. For example, in some embodiments, the reactive groups of the reactive multi-arm polymer are nucleophilic groups and the functional groups of the multifunctional compound group are electrophilic groups. In some embodiments, the reactive groups of the reactive multi-arm polymer are electrophilic groups and the functional groups of the multifunctional compound are nucleophilic groups. For example, the functional groups of the multifunctional compound may be electrophilic groups selected from imidazole esters, imidazole carboxylates, benzotriazole esters and imide esters, including N-hydroxysuccinimidyl esters. As another example, the functional groups of the multifunctional compound may be nucleophilic groups selected from amine groups and/or thiol groups.

In some embodiments, the reactive groups of the reactive multi-arm polymer and the functional groups of the multifunctional compound react with one another via an amide coupling reaction.

In various aspects, the present disclosure pertains to a crosslinkable system comprising (a) a first fluid composition comprising a reactive multi-arm polymer like that described above, which comprises a core (e.g., a polyol residue core or a silsesquioxane core, among others) and a plurality of polymer segments, each having a first end and a second end, and each formed from at least one type of unsaturated free-radical-polymerizable monomer, wherein the first end is linked to the core and the second end comprising a moiety that comprise a reactive group and, optionally, a hydrolysable ester group that is positioned between the reactive group and the polymer segment (the first composition may also contain nitroxide radicals as a result of the method by which it is produced, in certain embodiments) and (b) a second fluid composition comprising a multifunctional compound like that described above, which comprises functional groups that are reactive with the reactive end groups. In some embodiments, the reactive groups of the reactive multi-arm polymer are electrophilic groups and the functional groups of the multifunctional compound are nucleophilic groups. In some embodiments, the reactive groups of the reactive multi-arm polymer and the functional groups of the multifunctional compound react with one another via an amide coupling reaction.

In addition to the reactive multi-arm polymer, the first fluid composition may further comprise, for example, therapeutic agents and/or contrast agents, among other possibilities. In addition to the multifunctional compound, the second fluid composition may further comprise, for example, therapeutic agents and/or contrast agents, among other possibilities.

In various embodiments, the system will include one or more delivery devices for delivering the first and second fluid compositions to a subject. For example, the system may include a delivery device that comprises a first reservoir that contains the first fluid composition, a second contains the first second fluid composition. During operation, the first and second fluid compositions are dispensed from the first and second reservoirs, whereupon the first and second fluid compositions interact and crosslink with one another to form a hydrogel.

In particular embodiments, the system may include a delivery device that comprises a double-barrel syringe, which includes first barrel having a first barrel outlet, which first barrel contains the first fluid composition, a second barrel having a second barrel outlet, which second barrel contains the second fluid composition, a first plunger that is movable in first barrel, and a second plunger that is movable in second barrel.

In some embodiments, the device may further comprise a mixing section having a first mixing section inlet in fluid communication with the first barrel outlet, a second mixing section inlet in fluid communication with the second barrel outlet, and a mixing section outlet. In some embodiments, the device may further comprise a cannula or catheter tube that is configured to receive the first and second fluid compositions from the first and second barrels. For example, a cannula or catheter tube may be configured to form a fluid connection with an outlet of a mixing section by attaching the cannula or catheter tube to an outlet of the mixing section, for example, via a suitable fluid connector such as a luer connector.

As another example, the catheter may be a multi-lumen catheter that comprise a first lumen and a second lumen, a proximal end of the first lumen configured to form a fluid connection with the first barrel outlet and a proximal end of the second lumen configured to form a fluid connection with the second barrel outlet. In some embodiments, the multi-lumen catheter may comprise a mixing section having a first mixing section inlet in fluid communication with a distal end of the first lumen, a second mixing section inlet in fluid communication with a distal end of the second lumen, and a mixing section outlet.

During operation, when the first and second plungers are depressed, the first and second fluid compositions are dispensed from the first and second barrels, whereupon the first and second fluid compositions interact and crosslink to form a hydrogel, which is administered onto or into tissue of a subject. For example, the first and second fluid compositions may pass from the first and second barrels, into the mixing section via first and second mixing section inlets, whereupon the first and second fluid compositions are mixed to form an admixture, which admixture exits the mixing section via the mixing section outlet. In some embodiments, a cannula or catheter tube is attached to the mixing section outlet, allowing the admixture to be administered to a subject after passing through the cannula or catheter tube.

As another example, the first fluid composition may pass from the first barrel outlet into the first lumen of a multi-lumen catheter and the second fluid composition may pass from the second barrel outlet into the second lumen of the multi-lumen catheter. In some embodiments the first and second fluid compositions may pass from the first and second lumen into a mixing section at a distal end of the multi-lumen catheter via first and second mixing section inlets, respectively, whereupon the first and second fluid compositions are mixed in the mixing section to form an admixture, which admixture exits the mixing section via the mixing section outlet.

In additional aspects, the present disclosure pertains to crosslinked products of (a) a reactive multi-arm polymer like that described above, which comprises a core (e.g., a polyol residue core or a silsesquioxane core, among others) and a plurality of polymer segments, each having a first end and a second end, and each formed from at least one type of unsaturated free-radical-polymerizable monomer, wherein the first end is linked to the core and the second end comprising a moiety that comprise a reactive group and, optionally, a hydrolysable group that is positioned between the reactive group and the polymer segment and (b) a multifunctional compound that comprises functional groups that are reactive with the reactive end groups. Such crosslinked products may be formed in vivo (e.g., using a delivery device like that described above), or such crosslinked products may be formed ex vivo and subsequently administered to a subject. The crosslinked products may also contain nitroxide radicals in some embodiments.

In various embodiments, the reaction products of the functional groups of the multifunctional compound with the reactive end groups of the reactive multi-arm polymer comprise amide linkages.

In certain beneficial embodiments, the reactive groups of the reactive multi-arm polymers for use in the first fluid compositions of the above systems, and for use in forming the above crosslinked products (i.e., crosslinked products of the multi-arm polymers described herein with the multifunctional compounds as described herein), may be selected from imidazolyl esters, benzotriazole esters, imide esters, including N-hydroxysuccinimidyl esters, and imidazolyl carboxylates, among others.

In various embodiments, the multifunctional compound for use in the second fluid compositions of the above systems, and for use in forming the above crosslinked products, may be a polyamine. In general, polyamines suitable for use in the present disclosure include, for example, small molecule polyamines (e.g., containing at least two amine groups, for instance, from 3 to 20 amine groups, in some embodiments), comb polymers having amine side groups, and branched polymers having amine end groups, including dendritic polymers having amine end groups.

Particular examples of multifunctional amines which may be used as the multifunctional compound include trilysine, ethylenetriamine, diethylene triamine, hexamethylenetriamine, di(heptamethylene) triamine, di(trimethylene) triamine, bis(hexamethylene) triamine, triethylene tetramine, tripropylene tetramine, tetraethylene pentamine, hexamethylene heptamine, pentaethylene hexamine, dimethyl octylamine, dimethyl decylamine, and JEFFAMINE polyetheramines available from Huntsman Corporation, among others. Further particular examples of multifunctional amines include polypeptides including poly(L-lysine), chitosan, and poly(allyl amine), among others.

Figure 6:
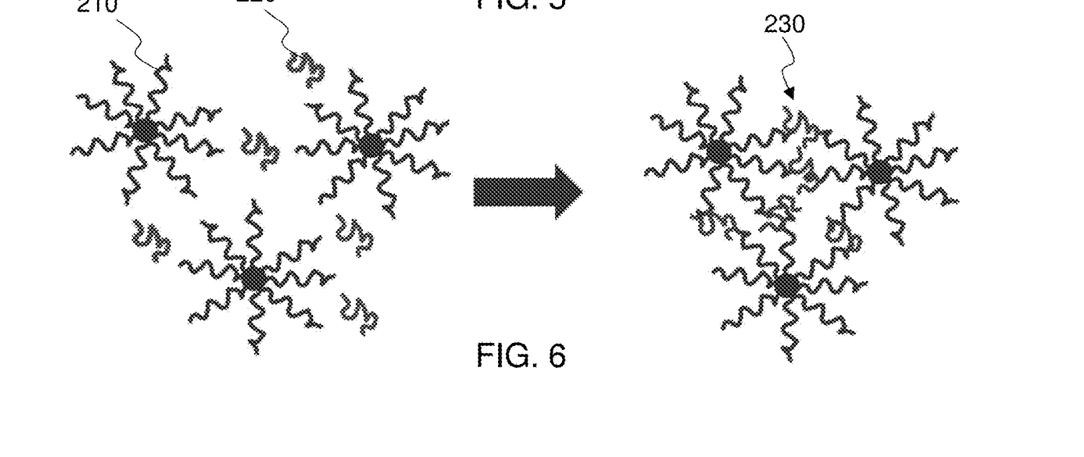
FIG. 6 is a schematic illustration of a method of crosslinking a reactive multi-arm polymer with a multifunctional crosslinking agent, in accordance with an embodiment of the present disclosure.

As shown schematically in FIG. 6, a reactive multi-arm polymer 210 like that described above (e.g., comprising a core such as a polyol residue core or a silsesquioxane core, among others, and a plurality of PVP segments, each PVP segment terminated with a succinimidyl-group) is crosslinked with a multifunctional compound 220 comprising functional groups that are reactive with the reactive groups of the multi-arm polymer 210 (e.g., a polyamine such as trilysine) to form a crosslinked product 230.

Compositions comprising the multi-arm polymers as described herein, as well as compositions comprising the cross-linked polymers described herein (i.e., crosslinked products of the multi-arm polymers described herein with the multifunctional compounds as described herein), can be used in a wide variety of biomedical applications, including medical devices, implants, and pharmaceutical compositions.

In various embodiments, compositions can be formed that include the multi-arm polymers described herein as well as one or more additional agents. In various embodiments, compositions can be formed that include the cross-linked polymers described herein as well as one or more additional agents.

Examples of such additional agents include therapeutic agents and imaging agents, among others.

Examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $FE^{(III)}$ and compounds (including chelates) containing the same, such as gadolinium ion chelated with diethylenetri-aminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) contrast agents for use in connection with x-ray fluoroscopy, including metals and metal compounds (e.g., metal salts, metal oxides, etc.), for instance, barium compounds, bismuth compounds and tungsten, among others, and iodinated compounds, among others, (e) radiocontrast agents, such as those based on the clinically important isotope $^{99m}Tc$, as well as other gamma emitters such as $^{123}I$, $^{125}I$, $^{131}I$, $^{111}In$, $^{57}Co$, $^{153}Sm$, $^{133}Xe$, $^{51}Cr$, $^{81m}Kr$, $^{201}Tl$, $^{67}Ga$, and $^{75}Se$, among others, (f) positron emitters, such as $^{18}F$, $^{11}C$, $^{13}N$, $^{15}O$, and $^{68}Ga$, among others, may be employed to yield functionalized radiotracer coatings, and (g) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and borondipyrromethane (BODIPY) analogs, among others.

Compositions in accordance with the present disclosure include lubricious compositions for medical applications, compositions for therapeutic agent release (e.g., by including one or more therapeutic agents in a matrix of the crosslinked polymers, by using the crosslinked polymers to encapsulate one or more therapeutic agents, etc.), implants, which may be formed ex vivo or in vivo (e.g., composition for use as tissue markers, compositions that act as spacers to reduce side effects of off-target radiation therapy, cosmetic compositions, etc.).

The invention claimed is:

1. A system comprising (a) a first composition comprising a multi-arm polymer comprising a core and a plurality of polymer segments having a first end that is covalently attached to the core and a second end comprising a moiety that comprises a reactive group, wherein the polymer segments comprise one or more hydrophilic aprotic NMP-polymerizable monomers, and wherein the multi-arm polymer comprises nitroxide radicals and (b) a second composition different from the first composition comprising a multifunctional compound that comprises functional groups that are different from the reactive groups of the multi-arm polymer, are reactive with the reactive groups of the multi-arm polymer, and form covalent bonds with the reactive groups of the multi-arm polymer;

wherein the moiety that comprises a reactive group further comprises a hydrolysable ester group; or wherein the core is a residue of a polyol selected from sugars, sugar alcohols, sugar oligomers, sugar alcohol oligomers, sugar polymers, and sugar alcohol polymers; or wherein the reactive groups of the reactive multi-arm polymer are electrophilic groups selected from imidazole esters, imidazole carboxylates, benzotriazole esters, and imide esters and the functional groups are nucleophilic groups selected from amine groups and/or thiol groups.

2. The system of claim 1, further comprising a delivery device.

3. A covalently crosslinked reaction product of (a) a multi-arm polymer comprising a core and a plurality of polymer segments having a first end that is covalently attached to the core and a second end comprising a moiety that comprises a reactive group, wherein the polymer segments comprise one or more hydrophilic aprotic NMP-polymerizable monomers, and wherein the multi-arm polymer comprises nitroxide radicals and (b) a multifunctional compound that comprises functional groups that are different from the reactive groups of the multi-arm polymer, are reactive with the reactive groups of the multi-arm polymer, and form covalent bonds with the reactive groups of the multi-arm polymer;

wherein the moiety that comprises the reactive group further comprises a hydrolysable ester group; or wherein the core is a residue of a polyol selected from sugars, sugar alcohols, sugar oligomers, sugar alcohol oligomers, sugar polymers, and sugar alcohol polymers; or wherein the reactive groups of the reactive multi-arm polymer are electrophilic groups selected from imidazole esters, imidazole carboxylates, benzotriazole esters, and imide esters and the functional groups are nucleophilic groups selected from amine groups and/or thiol groups.

4. The system of claim 1, wherein the moiety that comprises the reactive group further comprises the hydrolysable ester group.

5. The system of claim 1, wherein the polymer segments comprise N-vinyl pyrrolidone monomers.

6. The system of claim 1, wherein the polyol residue is the residue of the polyol selected from sugars, sugar alcohols, sugar oligomers, sugar alcohol oligomers, sugar polymers, and sugar alcohol polymers.

7. The covalently crosslinked reaction product of claim 3, wherein the moiety that comprises the reactive group further comprises the hydrolysable ester group.

8. The covalently crosslinked reaction product of claim 3, wherein the polymer segments comprise N-vinyl pyrrolidone monomers.

9. The covalently crosslinked reaction product of claim 3, wherein the polyol residue is the residue of the polyol selected from sugars, sugar alcohols, sugar oligomers, sugar alcohol oligomers, sugar polymers, and sugar alcohol polymers.

10. The system of claim 1, wherein the reactive groups of the reactive multi-arm polymer are the electrophilic groups selected from imidazole esters, imidazole carboxylates, benzotriazole esters, and imide esters and wherein the functional groups are the nucleophilic groups selected from amine groups and/or thiol groups.

11. The covalently crosslinked reaction product of claim 3, wherein the reactive groups of the reactive multi-arm polymer are the electrophilic groups selected from imidazole esters, imidazole carboxylates, benzotriazole esters, and imide esters and wherein the functional groups are the nucleophilic groups selected from amine groups and/or thiol groups.

* * * * *